(12) United States Patent
Russo et al.

(10) Patent No.: US 9,901,709 B2
(45) Date of Patent: Feb. 27, 2018

(54) ROLLED TIP RECOVERY CATHETER

(71) Applicant: Covidien LP, Mansfield, MA (US)

(72) Inventors: Patrick P. Russo, Vadnais Heights, MN (US); John C. Oslund, Cottage Grove, MN (US)

(73) Assignee: Covidien LP, Mansfield, MA (US)

( * ) Notice: Subject to any disclaimer, the term of this patent is extended or adjusted under 35 U.S.C. 154(b) by 486 days.

(21) Appl. No.: 14/268,228

(22) Filed: May 2, 2014

(65) Prior Publication Data
US 2014/0243884 A1    Aug. 28, 2014

Related U.S. Application Data

(63) Continuation of application No. 12/883,606, filed on Sep. 16, 2010, now Pat. No. 8,747,431, which is a
(Continued)

(51) Int. Cl.
*A61M 29/00* (2006.01)
*A61M 25/00* (2006.01)
*A61F 2/01* (2006.01)

(52) U.S. Cl.
CPC ......... *A61M 25/0082* (2013.01); *A61F 2/013* (2013.01); *A61M 25/0068* (2013.01); *A61M 25/0069* (2013.01); *A61M 25/0074* (2013.01); *A61F 2002/011* (2013.01); *A61F 2002/018* (2013.01); *A61F 2230/008* (2013.01);
(Continued)

(58) Field of Classification Search
CPC ............... A61F 2/013; A61F 2002/011; A61F 2002/9528; A61F 2002/9534; A61F 2/95; A61F 2230/0067; A61F 2002/018; A61F 2230/008; A61F 2230/0008; A61B 2017/22035; A61B 2017/3435; A61B 17/3417; A61B 17/3431; A61M 25/0067; A61M 25/0074; A61M 25/008; A61M 2025/0081; A61M 25/0082; A61M 2025/0079

See application file for complete search history.

(56) References Cited

U.S. PATENT DOCUMENTS 3,074,408 A * 1/1963 Chester ............ A61B 17/22031
606/127
4,324,262 A    4/1982 Hall
(Continued)

FOREIGN PATENT DOCUMENTS

DE    1566147 A1    7/1970
DE    2127125 A1 *  1/1973    ........... A61B 17/221
(Continued)

OTHER PUBLICATIONS

English Translation of DE1566147.
Abstract for JP 9-225035 (1 page).
Machine translation of DE 2 127 125 A1 (10 pages).

Primary Examiner — Anh Dang
Assistant Examiner — Erin Colello

(57) ABSTRACT

A distal tip for use with a medical catheter. The tip includes a member having a wall which defines a lumen therewithin. The wall has a portion at a distal end thereof, the portion curving inwardly toward an axis of the lumen. The lumen is provided with a diameter adaptable to accommodate a device to be recovered therewithin.

26 Claims, 3 Drawing Sheets

Related U.S. Application Data continuation of application No. 11/268,823, filed on Nov. 8, 2005, now Pat. No. 7,819,890, which is a continuation of application No. 10/074,740, filed on Feb. 12, 2002, now Pat. No. 6,979,343.

(60) Provisional application No. 60/268,773, filed on Feb. 14, 2001.

(52) U.S. Cl.
CPC .............. *A61F 2230/0008* (2013.01); *A61F 2230/0067* (2013.01); *A61M 2025/0079* (2013.01); *A61M 2025/0081* (2013.01)

(56) References Cited

U.S. PATENT DOCUMENTS

| | | | |
|---|---|---|---|
| 4,469,100 A | 9/1984 | Hardwick | |
| 4,531,943 A | 7/1985 | Van Tassel et al. | |
| 4,563,181 A | 1/1986 | Wijayarathna et al. | |
| 4,588,399 A | 5/1986 | Nebergall et al. | |
| 4,611,594 A * | 9/1986 | Grayhack | A61B 17/221 |
| | | | 606/127 |
| 4,863,442 A | 9/1989 | DeMello et al. | |
| 4,886,506 A | 12/1989 | Lovgren et al. | |
| 4,927,426 A * | 5/1990 | Dretler | A61B 17/221 |
| | | | 604/540 |
| 4,960,411 A | 10/1990 | Buchbinder | |
| 4,976,690 A | 12/1990 | Solar et al. | |
| 5,045,072 A | 9/1991 | Castillo et al. | |
| 5,078,702 A | 1/1992 | Pomeranz | |
| 5,102,415 A | 4/1992 | Guenther et al. | |
| 5,171,232 A | 12/1992 | Castillo et al. | |
| 5,217,468 A * | 6/1993 | Clement | A61B 10/02 |
| | | | 606/114 |
| 5,221,270 A | 6/1993 | Parker | |
| 5,234,416 A | 8/1993 | Macaulay et al. | |
| 5,300,032 A | 4/1994 | Hibbs et al. | |
| 5,300,048 A | 4/1994 | Drewes, Jr. et al. | |
| 5,308,342 A | 5/1994 | Sepetka et al. | |
| 5,318,032 A | 6/1994 | Lonsbury et al. | |
| 5,342,386 A | 8/1994 | Trotta | |
| 5,445,624 A | 8/1995 | Jimenez | |
| 5,447,503 A | 9/1995 | Miller | |
| 5,480,383 A | 1/1996 | Bagaoisan et al. | |
| 5,509,910 A | 4/1996 | Lunn | |
| 5,584,821 A | 12/1996 | Hobbs et al. | |
| 5,643,282 A | 7/1997 | Kieturakis | |
| 5,662,703 A | 9/1997 | Yurek et al. | |
| 5,769,830 A | 6/1998 | Parker | |
| 5,792,124 A | 8/1998 | Horrigan et al. | |
| 5,836,925 A | 11/1998 | Soltesz | |
| 5,846,251 A * | 12/1998 | Hart | A61B 17/22031 |
| | | | 606/127 |
| 5,911,715 A | 6/1999 | Berg et al. | |
| 6,093,173 A | 7/2000 | Balceta et al. | |
| 6,113,579 A | 9/2000 | Eidenschink et al. | |
| 6,159,230 A | 12/2000 | Samuels | |
| 6,174,318 B1 * | 1/2001 | Bates | A61B 17/221 |
| | | | 606/113 |
| 6,210,370 B1 * | 4/2001 | Chi-Sing | A61B 17/22032 |
| | | | 604/104 |
| 6,238,412 B1 * | 5/2001 | Dubrul | A61B 17/22 |
| | | | 606/108 |
| 6,245,089 B1 | 6/2001 | Daniel et al. | |
| 6,277,083 B1 | 8/2001 | Eggers et al. | |
| 6,290,710 B1 | 9/2001 | Cryer et al. | |
| 6,336,934 B1 | 1/2002 | Gilson et al. | |
| 6,485,501 B1 | 11/2002 | Green | |
| 6,544,279 B1 * | 4/2003 | Hopkins | A61F 2/01 |
| | | | 606/194 |
| 6,616,680 B1 * | 9/2003 | Thielen | A61F 2/013 |
| | | | 606/191 |
| 6,616,681 B2 | 9/2003 | Hanson et al. | |
| 6,663,651 B2 * | 12/2003 | Krolik | A61F 2/013 |
| | | | 128/899 |
| 6,695,834 B2 * | 2/2004 | Gellman | A61B 17/221 |
| | | | 606/114 |
| 6,878,153 B2 * | 4/2005 | Linder | A61F 2/013 |
| | | | 606/194 |
| 6,929,652 B1 * | 8/2005 | Andrews | A61F 2/013 |
| | | | 606/108 |
| 7,115,138 B2 | 10/2006 | Renati et al. | |
| 2002/0010476 A1 | 1/2002 | Mulholland et al. | |
| 2002/0058963 A1 * | 5/2002 | Vale | A61B 17/22031 |
| | | | 606/200 |
| 2002/0183781 A1 * | 12/2002 | Casey | A61B 17/22031 |
| | | | 606/198 |
| 2003/0114879 A1 | 6/2003 | Euteneuer et al. | |
| 2003/0176873 A1 | 9/2003 | Chernenko et al. | |
| 2004/0044359 A1 | 3/2004 | Renati et al. | |

FOREIGN PATENT DOCUMENTS

| | | | |
|---|---|---|---|
| DE | 2127125 A1 | 1/1973 | |
| DE | 2933266 A1 | 5/1981 | |
| JP | 9225035 | 9/1997 | |
| WO | WO-9601591 A1 | 1/1996 | |
| WO | WO 9803120 A1 * | 1/1998 | ....... A61B 17/22031 |
| WO | WO 9923952 A1 * | 5/1999 | ............. A61B 17/22 |
| WO | WO-9923976 A1 | 5/1999 | |
| WO | WO 0044428 A1 * | 8/2000 | ....... A61B 17/22031 |
| WO | WO-0044428 A1 | 8/2000 | |
| WO | WO-0108743 A1 | 2/2001 | |
| WO | WO-0112082 A1 | 2/2001 | |
| WO | WO 0112082 A1 * | 2/2001 | ....... A61B 17/22031 |
| WO | WO-0180776 A1 | 11/2001 | |
| WO | WO-0180777 A2 | 11/2001 | |
| WO | WO-0211627 A2 | 2/2002 | |

* cited by examiner

ROLLED TIP RECOVERY CATHETER

CROSS-REFERENCE TO RELATED APPLICATIONS

This application is a continuation of U.S. application Ser. No. 12/883,606, filed Sep. 16, 2010, which is a continuation of U.S. application Ser. No. 11/268,823, filed Nov. 8, 2005, now U.S. Pat. No. 7,819,890 B2, issued Oct. 26, 2010, which is a continuation of U.S. application Ser. No. 10/074,740, filed Feb. 12, 2002, now U.S. Pat. No. 6,979,343 B2, issued Dec. 27, 2005, which claims the benefit of, and priority to, U.S. Provisional Application Ser. No. 60/268,773, filed Feb. 14, 2001, the entire contents of each of the above-identified applications being incorporated herein by reference.

BACKGROUND OF THE INVENTION

1. Field of the Invention

The present invention relates generally to the field of medical catheters. More specifically, the present invention relates to recovery catheters used in distal embolic protection.

2. Description of the Related Art

Medical catheters are commonly employed for use in a lumen of a patient's body. The catheter enters the patient's body at an access site and is advanced through the lumen to a treatment site. The lumen may be in the patient's vascular system, such as that in a blood vessel, and the treatment site may be a stenosed region where a portion of the lumen is narrowed due to build-up of material on the lumen wall. Such narrowing is known as a stenosis.

The catheter may be guided to the treatment site through utilization of a guidewire. The guidewire typically is an elongated member having a distal end and a proximal end. The guidewire enters the patient's body at the access site and is advanced through the lumen to the treatment site. The distal end of the guidewire is the end nearest the treatment site, whereas the proximal end is the end nearest the access site. The guidewire may be positioned in proximity to the treatment site such that the distal end of the guidewire is moved to the proximal side of the treatment site (i.e., the side of the treatment site nearest the access site). The distal end of the guidewire may then cross the treatment site, thereby positioning the distal end of the guidewire on the distal side of the treatment site (i.e., the side of the treatment site farthest from the access site).

Generally, catheters comprise an elongated tubular body having a central lumen in which a guidewire can be received. The catheter is advanced along the guidewire for positioning at the treatment site. The catheter has a distal end that is advanced through the lumen of the patient's body to the treatment site.

The catheter body may have a diameter that makes it particularly difficult to advance the catheter across the treatment site if a stenosis has significantly narrowed the lumen. The prior art addresses this problem by providing a distal tip of the catheter which is tapered radially inwardly in the distal direction. Such a tapered distal tip allows for the catheter to be advanced through a narrowed portion of the lumen.

Another problem that may occur is that the catheter can become caught on a stent. A stent, generally, is a tubular wire structure that is positioned within a stenosis to maintain the lumen diameter. When a catheter is advanced across an area having a stent, the distal tip may engage an edge of the stent which can prevent further advancement of the catheter. Catheter advancement past a stent can be especially problematic when the stent is implanted in a curved vessel, or when the stent is underexpanded or incompletely deployed. This problem has been addressed by the prior art by rounding the distal tip or tapering the distal tip down to the approximate outer diameter of the guidewire in order to minimize the surface area available for engagement of the stent. This approach also provides for a gradual transition from the wire diameter to the catheter outer diameter, and tends to center the catheter in relation to the stent to facilitate stent crossing.

Some devices, such as embolic protection devices, may have a host wire that acts as a guidewire for other devices including catheters. An embolic protection device is a collapsible/expandable filter affixed to the distal portion of a guidewire. In the collapsed state, the embolic protection device is compressed toward the guidewire to give the device a smaller diameter so that it can be advanced within the lumen. In the expanded state the embolic protection device deploys outwardly from the guidewire such that it engages the wall of the lumen and acts as a filter by allowing fluid, such as blood, to pass therethrough while preventing emboli or particulate matter entrained in the fluid from passing therethrough. Emboli or particulate matter may become entrained in the fluid when a stenosis is being treated. Such particles of the stenosis may become dislodged due to contact with a treatment apparatus. Such treatments may include ablation procedures such as thrombectomy and atherectomy procedures, balloon angioplasty, stenting, and the like.

After treatment, the embolic protection device is typically collapsed in a manner wherein it maintains the captured emboli as the device is removed from the lumen. To prevent the release of the emboli back into the fluid, it is preferred to enclose the embolic protection device within a catheter. The collapsed embolic protection device has a proximal periphery that is greater than that of the outer diameter of the guidewire. Prior art catheters for receiving an embolic protection device have a relatively large diameter so as to receive the captured emboli containing protection device. Such catheters can be difficult to advance through a narrowed portion of a vessel or may become caught on a stent. If such catheters are provided with tapered tips, as described above, it becomes difficult to receive an emboli filled protection device within the catheter due to the small diameter of the tapered catheter tip. Alternatively, if prior art catheters are made small in diameter to facilitate stent crossing, it is possible that captured embolic material will be extruded through the distalmost part of the protection device filter during withdrawal of the emboli filled protection device into the small diameter catheter.

It would be advantageous to provide a catheter having a distal tip that allows passage of the catheter through a narrowed or stented portion of a lumen, while being able to receive an embolic protection device therein.

SUMMARY OF THE INVENTION

The present invention is an improved catheter for use in recovery of an embolic protection device. It is intended for use in a lumen of a patient's body such as a blood vessel. A distal tip of the catheter permits facile advance through a narrowed portion of the blood vessel, such as a stenosed region, and can conform in a manner to receive, for example, an embolic protection device having a diameter greater than the inner diameter of the distal tip.

An object of the invention is to provide a catheter that can cross stents or poorly deployed stents and yet can conform in a manner to receive an embolic protection device having a diameter greater than the inner diameter of the distal tip.

Another object of the invention is to provide a catheter that can cross stents or poorly deployed stents and yet can receive an embolic protection device without causing extruded emboli.

Yet another object of the invention is to provide a catheter with a large volume capacity that can cross stents or poorly deployed stents.

Yet another object of the invention is to provide a catheter tip that expands radially while receiving an embolic protection device having a diameter greater than the inner diameter of the distal tip.

The current invention comprises a tubular member having an inner diameter positionable over a guidewire having a device, such as an embolic protection device, carried proximate the distal end thereof. The distal tip is formed of a compliant material and has an inner diameter less than the diameter of a deployed embolic protection device. The material adapts to conformingly receive the protection device therein as the device is drawn into a lumen in the distal tip.

A preferred embodiment of the present invention comprises a distal tip attached to a main catheter body. The distal tip is defined by a body having a taper decreasing in a direction toward the distal end. The tubular body defines a wall forming a lumen therein. At the distal end, the wall of the body curves inward toward the lumen, thus forming a rolled tip. The distal tip is made of a compliant material that adapts to conformingly receive a device such as an embolic protection device.

DESCRIPTION OF THE DRAWING FIGURES

DETAILED DESCRIPTION OF THE INVENTION

Figure 1:
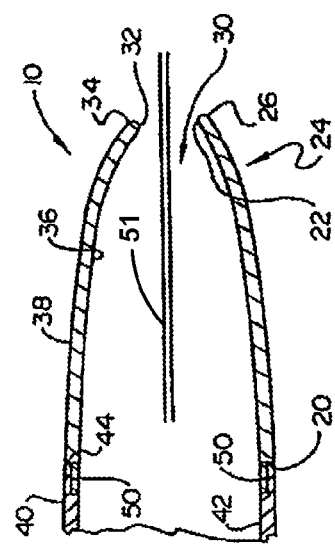
FIG. 1 is a side sectional view of a distal tip in accordance with the present invention mounted to the distal end of a catheter.

The device shown in FIG. 1 is suitable for use on a medical recovery catheter. The distal tip 10 comprises a tapered member. The member has a wall 34 that defines a lumen 30. The lumen 30 extends through the length of the distal tip 10. The lumen 30 extends from the proximal end 20 of the distal tip 10 to the distal end 24 of the distal tip 10 to form an aperture through the distal tip 10. The distal end 24 is the end located farthest from the attachment to the main catheter body 40, and the proximal end 20 is the end located nearest the catheter body 40.

A catheter body 40, suitable for use with the present invention, is a tubular member that has a lumen therethrough. The catheter lumen is in communication with the lumen 30 of the distal tip 10. The catheter lumen 42 is in communication with the lumen 30 of the distal tip 10 when the distal end 44 of the catheter is connected to the proximal end 20 of the distal tip 10. The catheter body may optionally contain a radiopaque marker band 50 in the general vicinity of the distal end 44 of the catheter. The radiopaque marker band may be entirely within the catheter body 40, entirely within the proximal portion of the distal tip, or any combination thereof.

Figure 2:
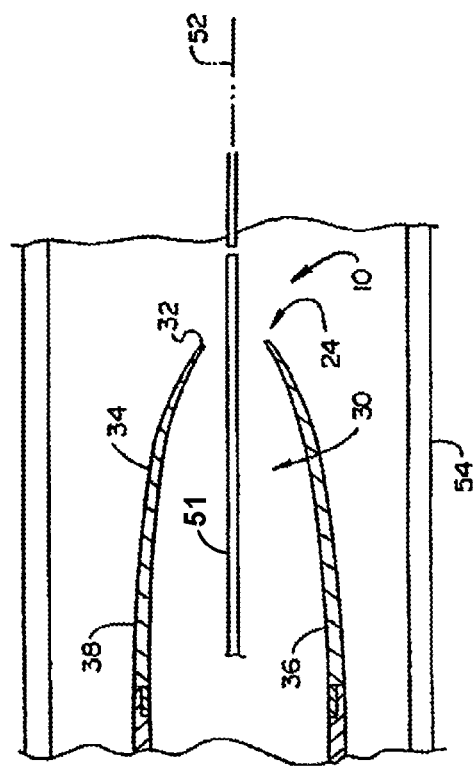
FIG. 2 is a view, similar to FIG. 1, illustrating an alternative embodiment.

The wall 34 of the distal tip 10 has a given thickness. The wall thickness can be uniform or be tapered. In one embodiment, the wall 34 has a taper decreasing to a lesser thickness as the wall progresses in the distal direction as shown in FIG. 2.

The lumen 30 of the distal tip 10 can have a uniform diameter along the length of the distal tip 10 or it may be tapered. In one embodiment, the lumen of the distal tip 30 tapers narrowingly in the distal direction. Thus, the lumen diameter can decrease as it progresses in the distal direction.

The distal end 24 of the distal tip 10 can have a rolled tip as at 32. The portion of the wall 34 at the distal end 24 of the distal tip 10 can be rolled inward toward the axis 52 of the lumen 30 to form the rolled tip 32.

The wall 34 of distal tip 10 has an inside surface 36 and an outer surface 38. At the rolled tip 32, end 22 is shown as facing inwardly toward the lumen 30. The end 22 is facing generally radially inwardly. The outer surface 38, over most of the length of the distal tip 10, faces generally radially outwardly. However, at the rolled tip 32, the outer surface 38 is curved so as to face in the distal direction to define a distal contact surface 26.

The present invention can be used in the lumen of a human body, such as in a blood vessel 54. The rolled tip 32 is especially designed for crossing a stented or otherwise constricted region of a blood vessel 54. A stent is a generally tubular member having a wire wall defining the boundary of the blood vessel lumen. The catheter must pass through the lumen defined within the stent in order to cross the stented region. As a catheter in accordance with the prior art is advanced within the blood vessel, the distal end of the catheter can become caught against an axial end of the stent. This is particularly true at a curve in the blood vessel 54, or when the stent is underexpanded or incompletely deployed. More specifically, the end of the catheter may engage an axial end of the stent. This can prevent the catheter from being able to advance farther into the blood vessel 54. Similar problems may occur in a constricted or stenosed region of a blood vessel.

The rolled tip configuration in accordance with the present invention can prevent such problems. A catheter utilizing the distal tip 10, having a rolled tip 32 described herein, is inserted into a blood vessel. The distal tip 10 is advanced to a stented region of the blood vessel. The rolled tip 10 is curved, as previously discussed, such that the outer portion of the wall 34 at the rolled tip 32 defines contact surface 26. As the distal tip 10 is advanced through the region, the contact surface 26 of the rolled tip 32 may engage a stent. The rolled tip 32 prevents the distal tip 10 from becoming impassibly engaged with the stent. As the distal tip 10 is urged across the stented region, the rolled tip 32 may contact the stent, but it will deflect from the point of contact and be urged away from the stent. Thus, where the outer surface 38 contacts the stent, the distal tip 10 can continue advancing past the stent as a result of non-engagement with the axial end of the stent and allowing the distal tip 10 to continue advancing within the blood vessel 54.

The distal tip 10 can also function to capture, for example, a protection device 58 within the lumen 30. Lumen 30 is of a given diameter. The distal tip 10 is connected to a catheter such that the distal tip lumen 30 is in smooth communication with a catheter lumen 42.

A device 58 to be captured within the lumen 30 might be, for example, an embolic protection device. A guidewire 51 extends proximal with respect to the protection device 58, extending through the lumen 30 of the distal tip 10 and catheter 40. The device is typically positioned distal to the distal tip 10 and is secured to the guidewire 51. The protection device 58 has a diameter that is typically greater than that of the distal tip distal end 24.

Figure 3:
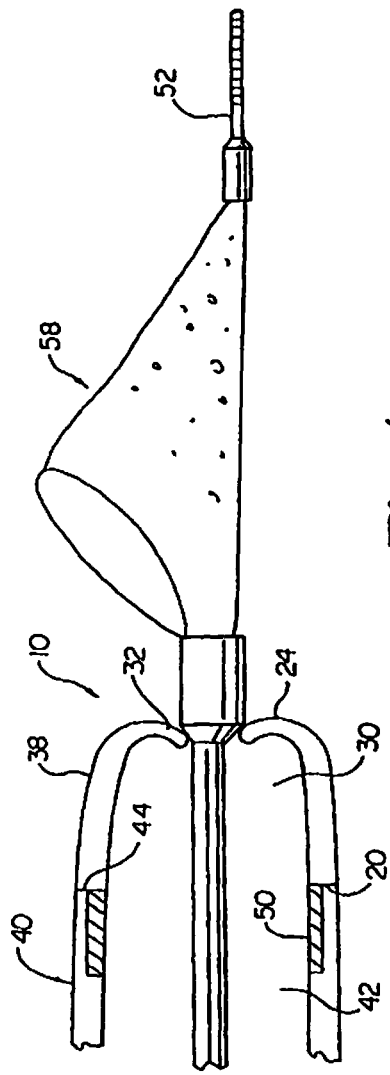
FIG. 3 is a view of the present invention illustrating a distal protection device beginning to be drawn therewithin.
Figure 4:
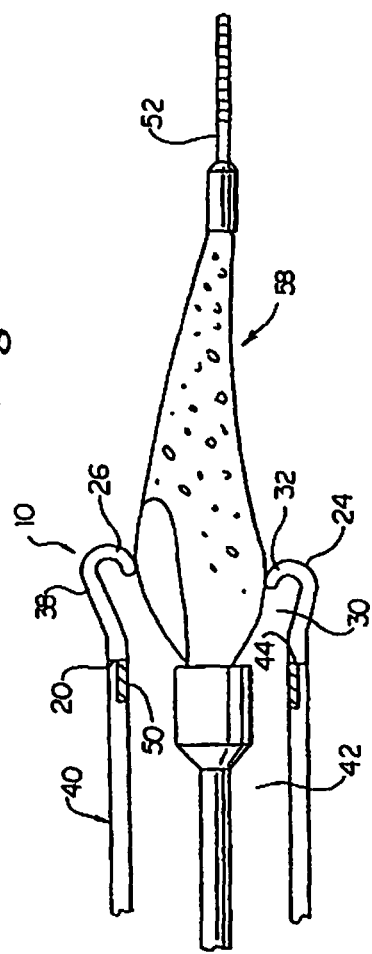
FIG. 4 is a view similar to FIG. 3 illustrating the protection device being drawn into the distal tip and deforming the distal end thereof.
Figure 5:
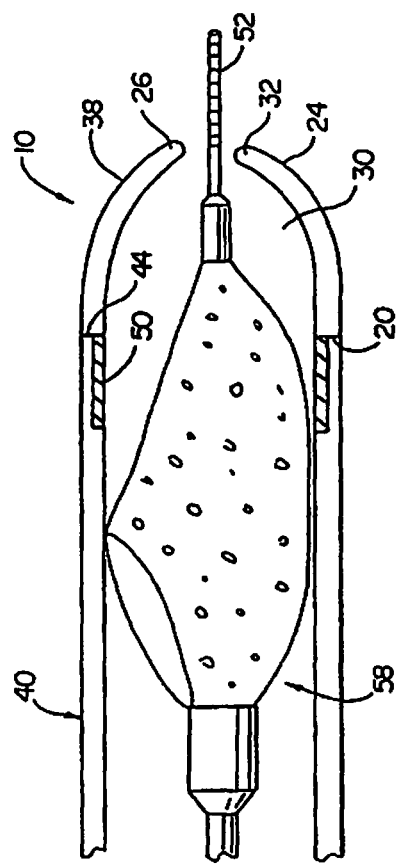
FIG. 5 is a view similar to FIGS. 3 and 4 illustrating the distal tip having captured the protection device.

Again, the distal tip 10 is made of a compliant material such that the protection device 58 can be facilely received into the distal tip lumen 30. As the protection device 58 is drawn toward the distal tip 10, it will first contact the rolled tip 32 at the contact surface 26. The rolled tip 32 may be urged elastically inward as the device enters the lumen 30 (FIG. 3). After the device 58 has been fully drawn in the proximal direction relative to distal tip 10, the rolled tip 32 reaches a point where it ceases to be engaged by the device, and it will return to its undeflected configuration (FIG. 5). As the device 58 is being drawn into the lumen 30, however, the lumen 30 will adapt to conformingly hold the device 58 therein and rolled tip 32 will expand radially to accommodate the periphery of the device (FIG. 4). The device 58 will eventually have become fully housed within the catheter lumen, and the distal tip 10 returns, as discussed above, substantially to its original configuration.

It will be understood that resilient material forming the distal tip 10 prevents the escape of emboli when the embolic protection device 58 is captured. At least a portion of the wall of the distal tip 10 closely encompasses the periphery of the protection device 58 and assumes the shape of the periphery. As a result, emboli are prevented from passing between the periphery of the protection device 58 and the wall of the distal tip 10. Emboli within the protection device 58 are prevented from being released back into the blood vessel. Once the protection device 58 has been received within the catheter lumen, the distal tip 10 resumes substantially the size, shape, and dimensions of its original configuration.

The distal tip 10 is a soft, deformable tip made of an elastic, compliant material. Suitable materials for making the distal tip include thermoplastic polymer and polymer blends or thermoset polymers such as silicone or silicone blends with a low durometer. One such material is a 35/40 D Pebax blend. Any other appropriate compliant materials may, however, be used.

The polymer tip may be filled with radiopaque materials such as barium sulphate, bismuth subcarbonate, tungsten powder, and the like. The tip 10 can be molded or formed using a heated die or in any other such method. Radiofrequency induction heating, electrical resistance heating, conduction heating, or any other method may be used. The preferred dimensions of the formed tip 10 will, of course, depend on the dimensions of the catheter. For example, a range of catheter sizes is from 4.2 F to 6.0 F, with corresponding inner diameters of 0.042 inches and 0.062 inches, respectively. These catheters might have distal tips with rolled distal inner diameter's of 0.025 to 0.050 inches, respectively. The diameter of the distal tip lumen 30 can be constant or tapered toward the distal end. The tip 10 may be attached to the catheter by any appropriate method such as a unitary design, heating, adhesive bonding, or molding.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims.

The invention claimed is:

1. A method of retrieving a medical device from within a body vessel, the method comprising:
    advancing a retrieval catheter into the body vessel with a distal tip of the retrieval catheter in an original, undeflected configuration;
    contacting the medical device with the distal tip of the retrieval catheter;
    drawing the medical device into the retrieval catheter such that the distal tip of the retrieval catheter is moved proximally and then subsequently moved radially outward in relation to a central longitudinal axis of the retrieval catheter; and
    after the distal tip of the retrieval catheter is moved radially outward in relation to the central longitudinal axis of the retrieval catheter, drawing the medical device further into the retrieval catheter such that the distal tip of the retrieval catheter is moved radially inward in relation to the central longitudinal axis of the retrieval catheter and returned substantially to the original, undeflected configuration.

2. The method of claim 1, wherein drawing the medical device further into the retrieval catheter such that the distal tip of the retrieval catheter is moved radially inward in relation to the central longitudinal axis of the retrieval catheter and returned substantially to the original, undeflected configuration includes moving the distal tip of the retrieval catheter distally.

3. The method of claim 1, wherein drawing the medical device into the retrieval catheter includes reducing a distance between a distal end of the retrieval catheter and a proximal end of the retrieval catheter along the central longitudinal axis of the retrieval catheter.

4. The method of claim 1, wherein drawing the medical device into the retrieval catheter includes positioning a portion of the distal tip within a lumen defined by the retrieval catheter.

5. The method of claim 1, wherein advancing the retrieval catheter into the body vessel includes advancing the retrieval catheter into a blood vessel.

6. The method of claim 1 further including positioning a guidewire within the body vessel.

7. The method of claim 6, wherein advancing the retrieval catheter into the body vessel includes advancing the retrieval catheter over the guidewire.

8. The method of claim 1 further including remotely visualizing the retrieval catheter within the body vessel.

9. The method of claim 8, wherein remotely visualizing the retrieval catheter within the body vessel includes visualizing a radiopaque portion of the retrieval catheter.

10. The method of claim 9, wherein visualizing the radiopaque portion of the retrieval catheter includes visualizing a radiopaque marker located adjacent the distal tip.

11. The method of claim 1, wherein the distal tip of the retrieval catheter is formed from a resilient material, and wherein moving the distal tip of the retrieval catheter radially inward comprises fully housing the medical device within a lumen of the retrieval catheter.

12. The method of claim 1, wherein the distal tip has a first inner diameter at a distal end of the distal tip and a second inner diameter at a proximal end of the distal tip, the first inner diameter being smaller than the second inner diameter.

13. The method of claim 12, wherein the medical device has an outer diameter greater than the first inner diameter.

14. The method of claim 1, wherein the distal tip defines a lumen that tapers in a distal direction, and wherein drawing the medical device into the retrieval catheter comprises drawing the medical device into the lumen.

15. The method of claim 1, wherein drawing the medical device into the retrieval catheter such that the distal tip of the retrieval catheter is moved proximally comprises drawing the medical device into the retrieval catheter such that the distal tip of the retrieval catheter is moved proximally inward.

16. A method of retrieving a medical device from within a body vessel, the method comprising:

advancing a retrieval catheter into the body vessel;

contacting the medical device with a distal tip of the retrieval catheter; and drawing the medical device into the retrieval catheter such that the distal tip of the retrieval catheter is moved proximally and then subsequently moved radially outward in relation to a central longitudinal axis of the retrieval catheter, wherein drawing the medical device into the retrieval catheter includes drawing an embolic protection device into the retrieval catheter; and after the distal tip of the retrieval catheter is moved radially outward in relation to the central longitudinal axis of the retrieval catheter, drawing the medical device further into the retrieval catheter such that the distal tip of the retrieval catheter is moved radially inward in relation to the central longitudinal axis of the retrieval catheter.

17. A method of retrieving a medical device from within a body vessel, the method comprising:

advancing a retrieval catheter into the body vessel with a distal tip of the retrieval catheter in an original, undeflected configuration;

contacting the medical device with the distal tip of the retrieval catheter;

drawing the medical device into the retrieval catheter such that the distal tip of the retrieval catheter is moved proximally and a distance defined between a distal end of the retrieval catheter and a proximal end of the retrieval catheter along a central longitudinal axis of the retrieval catheter is reduced; and after the distal tip of the retrieval catheter is moved proximally, drawing the medical device further into the retrieval catheter such that the distal tip of the retrieval catheter is returned substantially to the original, undeflected configuration.

18. The method of claim 17, wherein drawing the medical device into the retrieval catheter includes positioning a portion of the distal tip within a lumen defined by the retrieval catheter.

19. The method of claim 17, wherein drawing the medical device into the retrieval catheter includes deflecting the distal tip of the retrieval catheter.

20. The method of claim 19, wherein deflecting the distal tip of the retrieval catheter includes moving the distal tip of the retrieval catheter radially outward in relation to a central longitudinal axis of the retrieval catheter.

21. The method of claim 17, wherein advancing the retrieval catheter into the body vessel includes advancing the retrieval catheter into a blood vessel.

22. The method of claim 17, wherein the distal tip has a first inner diameter at a distal end of the distal tip and a second inner diameter at a proximal end of the distal tip, the first inner diameter being smaller than the second inner diameter.

23. The method of claim 22, wherein the medical device has an outer diameter greater than the first inner diameter.

24. The method of claim 17, wherein the distal tip defines a lumen that tapers in a distal direction, and wherein drawing the medical device into the retrieval catheter comprises drawing the medical device into the lumen.

25. The method of claim 17, wherein drawing the medical device further into the retrieval catheter such that the distal tip of the retrieval catheter is returned substantially to the original, undeflected configuration includes moving the distal tip of the retrieval catheter distally in relation to the central longitudinal axis of the retrieval catheter.

26. The method of claim 17, wherein drawing the medical device into the retrieval catheter such that the distal tip of the retrieval catheter is moved proximally comprises drawing the medical device into the retrieval catheter such that the distal tip of the retrieval catheter is moved proximally inward.

* * * * *